United States Patent [19]

Bowen

[11] Patent Number: 5,401,783
[45] Date of Patent: Mar. 28, 1995

[54] ADHESION-PROMOTING AGENTS INCORPORATING POLYVALENT CATIONS

[75] Inventor: Rafael L. Bowen, Gaithersburg, Md.

[73] Assignee: American Dental Association Health Foundation, Gaithersburg, Md.

[21] Appl. No.: 158,115

[22] Filed: Nov. 24, 1993

Related U.S. Application Data

[62] Division of Ser. No. 898,516, Jun. 15, 1992, Pat. No. 5,270,351.

[51] Int. Cl.$^6$ .......................... A61K 6/08; A61C 5/00
[52] U.S. Cl. ................................ 523/116; 433/228.1; 106/35; 523/118
[58] Field of Search .............................. 523/116, 118; 433/228.1; 206/635; 106/35

[56] References Cited

U.S. PATENT DOCUMENTS

| | | | |
|---|---|---|---|
| 30,709 | 3/1893 | Chow et al. | 424/423 |
| Re. 33,161 | 2/1990 | Brown et al. | 423/308 |
| Re. 33,221 | 5/1990 | Brown et al. | 423/308 |
| 3,066,112 | 11/1962 | Bowen | 260/41 |
| 3,194,783 | 7/1965 | Bowen | 260/41 |
| 3,200,142 | 8/1965 | Bowen | 260/486 |
| 3,785,832 | 1/1974 | Bowen | 106/35 |
| 4,224,023 | 9/1980 | Cheung | 433/216 |
| 4,514,527 | 4/1985 | Bowen | 523/115 |
| 4,521,550 | 6/1985 | Bowen | 523/116 |
| 5,188,670 | 2/1993 | Constantz | 118/667 |
| 5,231,169 | 7/1993 | Constantz et al. | 530/356 |

(List continued on next page.)

OTHER PUBLICATIONS

Dental Adhesives, p. 2, May 1990, Reality Publishing Co., Houston, Tex.

(List continued on next page.)

Primary Examiner—Paul R. Michl
Assistant Examiner—LaVonda R. DeWitt
Attorney, Agent, or Firm—Allegretti & Witcoff, Ltd.

[57] ABSTRACT

Materials and methods for preparing the surface of dentin, enamel, or other natural or industrial substrates containing or capable of binding metallic ions, for adhesion of composite materials or resins, are disclosed. Preferably, the substrate is treated with an aqueous solution comprising at least one acid, acidic salt, or chelating or sequestering agent. The resultant surface is then treated with a solution comprising a solvent and at least one adhesion-promoting agent selected from the group consisting of N-phenylglycine (NPG) and derivatives and analogues thereof, and other amino acids in the form of salts and complexes of these compounds with at least one species of divalent or polyvalent cation, or diamine or polyamine, wherein the divalent and polyvalent cations are preferably selected from the group consisting of alkaline earth elements, iron, aluminum, zinc, barium, chromium, manganese, cobalt, copper, and molybdenum, and wherein the divalent and polyvalent salts and complexes for each mixture comprise between 1 and 100% of the total mixture. Finally, a solution is applied which contains at least one monomer selected from the group consisting of (1) reaction products of dianhydrides with molecules containing at least one methacrylate, acrylate or other polymerizable group and also one reactive hydroxyl group, or primary or secondary amino group, (2) 4-methacryloxyethyltrimelliticanhydride and its dicarboxylic acid hydrolysis derivative, and (3) other compounds containing at least one group or moiety capable of free radical polymerization and at least one aromatic ring or moiety containing electron-withdrawing substituents that do not interfere with free radical polymerization, in the presence of a solvent, wherein the solvent comprises between 0 and 99.9% of the liquid. Alternative embodiments are also set forth.

39 Claims, No Drawings

U.S. PATENT DOCUMENTS

| | | | |
|---|---|---|---|
| 4,588,756 | 5/1986 | Bowen | 523/116 |
| 4,599,085 | 7/1986 | Riess et al. | 623/16 |
| 4,659,751 | 4/1987 | Bowen | 523/116 |
| 4,880,610 | 11/1989 | Constantz | 423/305 |
| 4,964,911 | 10/1990 | Ibsen et al. | 523/118 |
| 5,034,059 | 7/1991 | Constantz | 106/161 |
| 5,047,031 | 9/1991 | Constantz | 606/77 |
| 5,053,212 | 10/1991 | Constantz et al. | 423/305 |
| 5,129,905 | 7/1992 | Constantz | 606/76 |
| 5,164,187 | 11/1992 | Constantz et al. | 424/423 |
| 5,178,845 | 1/1993 | Constantz et al. | 423/305 |

OTHER PUBLICATIONS

Information Disclosure Statement and Supplemental Information Disclosure Statement of Ser. No. 07/791,999.

Constantino and Friedman et al., "Hydroxyapatite Cement: I. Basic Chemistry and Histologic Properties," 117 Arch. Otolaryngol. Head Neck Surg. 379 (Apr. 1991).

Bostrom et al., "Reconstruction of Craniotomy Burr-Holes With Autologous Bone Blugs (sic) Made by a New Hole-Saw," 105 Acta Neurochir. 132 (1990).

"Titanium Micro System", Leibinger GmbH 1992.

"Dumbach Titan Mesh-System" (DTM) of Osw. Leibinger GmbH (1990).

Chow et al., "Self-Setting Calcium Phosphate Cements," 179 Mat. Res. Soc. Symp. Proc. 3 (1991).

ADHESION-PROMOTING AGENTS INCORPORATING POLYVALENT CATIONS

This invention was supported in part by USPHS Research grant DE-05129 to the American Dental Association Health Foundation from the National Institute of Dental Research, Bethesda, Md. The government may have certain rights to this invention.

This application is a divisional application of U.S. patent application Ser. No. 07/898,516, filed Jun. 15, 1992, now U.S. Pat. No. 5,270,351, issued Dec. 14, 1993.

BACKGROUND OF THE INVENTION

1. Field of the Invention

This invention relates to methods of improving adhesive bonding of acrylic and other resins to industrial and dental substrates, and more particularly to dental restoration methods and methods of improving adhesion of composite dental materials to dentin and enamel. More specifically, methods for durable adhesive bonding of composite resins to dentin are disclosed with the objects of improving treatment of cervical erosions, root caries, and other dental conditions and of eliminating much mechanical cutting of dentin now required for retention of restorations.

The complete disclosures of U.S. Pat. No. 4,514,527, No. 4,521,550, No. 4,588,756 and No. 4,659,751, and U.S. patent application Ser. No. 07/791,999, filed Nov. 14, 1991 are expressly incorporated herein by reference.

2. Description of the Prior Art

For many years, advances in the study of methods of adhesive bonding of composite materials to hard tooth tissues have evolved by small increments. Previous experiments in adhesive bonding of composite materials to dentin demonstrated beneficial effects from cleansers, mordants, and adhesion promoting coupling agents; see, for example, Bowen, R. L., "Adhesive Bonding of Various Materials to Hard Tooth Tissues. XXII. The Effects of a Cleanser, Mordant, and PolySAC on Adhesion Between a Composite Resin and Dentin", 59 J. Dent. Res. 809–814 (1980); Bowen, R. L., "Use of Polyfunctional Surface-Active Comonomer and Other Agents to Improve Adhesion Between a Resin or Composite Material and a Substrate", U.S. Pat. No. 4,251,565, February 1981; Bowen, R. L., "Adhesive Bonding of Various Materials to Hard Tooth Tissues. XIX. Solubility of Dentinal Smear Layer in Dilute Acid Buffers", 28 Int'l Dent. J. 97–104 (1978); Bowen, R. L., "Adhesive Bonding of Various Materials to Hard Tooth Tissues. VII. Metal Salts as Mordants for Coupling Agents", in Moskowitz, H.; Ward, G.; & Woolridge, E., (eds.); Dental Adhesive Materials, pp. 205–221, Proceedings from Symposium held Nov. 8–9, 1973 at the Hunter-Bellevue School for Nursing, New York City, Prestige Graphic Services (1974).

The rationale for using a surface-active comonomer as a coupling agent to improve bonding has been supported by previous data. Bowen, R. L., "Adhesive Bonding of Various Materials to Hard Tooth Tissues. II. Bonding to Dentin Promoted by a Surface-Active Comonomer", 44 J. Dent. Res. 895–902 (1965); Bowen, R. L., "Adhesive Bonding of Various Materials to Hard Tooth Tissues. III. Bonding to Dentin Improved by Pretreatment and the Use of a Surface-Active Comonomer", 44 J. Dent. Res. 903–905 (1965); Bowen, R. L., "Adhesive Bonding of Various Materials to Hard Tooth Tissues. IV. Bonding to Dentin, Enamel, and Fluorapatite Improved by the Use of a Surface-Active Comonomer", 44 J. Dent. Res. 906–911 (1965); Bowen, R. L., "Adhesive Bonding of Various Materials to Hard Tooth Tissues V. The Effect of a Surface-Active Comonomer on Adhesion to Diverse Substrates", 44 J. Dent. Res. 1369–1373 (1965). The addition reaction product of N-phenylglycine and glycidyl methacrylate (NPG-GMA) and the addition reaction product of N-phenylglycine and p-chlorophenylglycidyl ether (NPG-CGE) are disclosed, respectively, as vehicles to improve adhesive bonding to a limited extent in Bowen, U.S. Pat. No. 3,200,142, Aug. 10, 1965, and in Bowen, British Pat. No. 1,448,134 and U.S. Pat. No. 3,785,832, Jan. 15, 1974.

Methods for preparing surfaces, such as dentin, enamel, or other natural or industrial substrates, more particularly surfaces containing or capable of binding metallic ions, for adhesion of composite materials or resins have been disclosed in U.S. Pat. No. 4,514,527, No. 4,521,550, No. 4,588,756 and No. 4,659,751 to Bowen. These methods include, inter alia, treating such surfaces with acidic aqueous solutions of inorganic acids, polycarboxylic acids, and metal salts of such acids comprised of transition metals capable of changing valence states, washing away the dissolved debris, and then treating the resulting surfaces with adhesion-promoting agents such as N-arylglycine and derivatives, including derivatives having at least one polymerizable moiety, and adhesive bonding monomer agents, such as the reaction products of dianhydrides with molecules containing at least one methacrylate, acrylate or other polymerizable group and also one reactive hydroxyl group, or primary or secondary amino group; 4-methacryloxyethyltrimelliticanhydride and its dicarboxylic acid hydrolysis derivative; and/or other compounds containing at least one group or moiety capable of free radical polymerization and at least one aromatic ring or moiety containing electron-withdrawing substituents that do not interfere with free radical polymerization.

In the prior art, amino acids, including N-arylglycine and derivatives and including derivatives having at least one polymerizable moiety, were in the acidic form (i.e., the carboxyl groups being protonated by the low pH of the solutions) and/or in the form of a monovalent salt of an alkali element, such as sodium or potassium, or as a readily-hydrolyzable lower alkyl or aryl ester (see U.S. Pat. No. 4,659,751, col. 6, line 58). When these amino acids are in the protonated or zwitterionic form, they are subject to undesirable degradation, especially when in solution, between the time of manufacture and utilization. When they are in the form of monovalent alkali metal salts, they cannot provide "molecular ionic bridging" as described hereinbelow. In particular, mixtures of alkali metal salts with protonated or zwitterionic forms of these agents, as described in U.S. Pat. No. 4,964,911, suffer from both of these disadvantages.

Although an acid-etch technique had been effective in beneficiating the bonding of composite and unfilled resins to enamel of teeth, no method had existed until recently for achieving strong adhesive bonding between composite and unfilled resins and dentin to the same useful degree. Many investigators have been attempting to achieve significantly enhanced adhesive bonds to both dentin and enamel and various other substrates for well over twenty-five years with limited success. The present invention represents an improvement in this area of technology.

SUMMARY OF THE INVENTION

It has recently been discovered that the cleansing and "mordanting" procedures used in the prior art to remove the disturbed, smeared surface layer and/or pellicle and plaque from dentin surfaces, or the incidental and sometimes unrecognized effects of rinsing off phosphoric or other acids used to etch adjacent enamel, leave a hydrated, organic-rich demineralized surface layer even when these solutions contain polyvalent cations. Microscopy indicates that this demineralized layer averages about 1 micrometer in thickness and acts as a weak boundary layer limiting the adhesive bond strengths obtainable by contemporary bonding systems. Bonding strength of synthetic resins to such substrates depends on the strength and hardness of the interfacial regions, which is in turn dependent upon the degree of linking, crosslinking and chain formation both within the substrate materials and between the substrate material and the applied adhesive bonding agents. The effectiveness of the adhesive bonding agents mentioned herein depends primarily on their acidic functionalities interacting with basic di- (divalent) or polyvalent cations (such as calcium in the case of the calcified portion of tooth surfaces). It is these basic cations that are removed by the aforesaid cleansing procedures. Since the organic portions of tooth substance are acidic in nature (which allows them to interact strongly with the quasi-basic hydroxyapatite-like mineral components in the natural tooth composition), adhesive bonding agents comprised of acidic functionalities or with monovalent salts of these functionalities cannot interact well with the acidic demineralized organic layer of surfaces that have been demineralized in the cleansing process.

I have now discovered that di- and polyvalent salts or complexes of certain adhesion-promoting agents, defined herein as N-phenylglycine (NPG) and derivatives and analogues thereof (such as NTG-GMA, the adduct of N(p-tolyl)glycine and glycidyl methacrylate, and others, described below), are soluble in organic solvents, and that these di- and polyvalent cation salts or complexes can carry with them into this demineralized surface zone replacement ions for the natural divalent calcium cations that are removed in the cleansing process. The significance of di- and polyvalent cations is that they have bridging and linking properties not shared by monovalent cations such as hydrogen ions or by cations of alkali metal elements (lithium, sodium, potassium, cesium, and rubidium). The present invention is believed to solve the problem of the adhesive-resistant quality of the demineralized boundary layer of cleansed dentin and other surfaces by supplying, incorporated as part of the adhesion-promoting agents (such as N-phenylglycine, its derivatives, and other amino acids), di- and polyvalent cations that can participate in ionic bond interactions (1) between acidic groups within the demineralized organic superficial layer; (2) between acidic groups of the substrate organic layer and acidic groups of the adhesion-promoting agents; (3) between the carboxyl groups of acidic adhesive resin monomers, defined herein as polymerizable monomers containing acidic groups or moieties and that do not contain basic amino groups, such as PMDM (the reaction product of pyromellitic dianhydride and hydroxyethyl methacrylate), its analogues and others including those described herein, in the prior art and in the co-pending application (Ser. No. 07/791,999, "Hydrophilic Adhesive Monomers and Polymers Made Therefrom"); (4) between the carboxyl groups of adhesion-promoting agents described herein (for example, NTG-GMA) and the carboxyl groups of adhesive resin monomers (for example, PMDM) and their analogues; and (5) between the multiple carboxyl groups of adhesive resin monomer molecules (e.g., PMDM) and their analogues, and (6) other polymerizable monomers containing acidic groups or moieties.

The present invention comprises materials and methods that increase the storage and color stability and the previously obtainable strengths of adhesive bonds between composite materials or resins and dentin in vitro, and can yield effective bonding between these materials or resins and enamel and other substrates. Thus, it is an advantage of this invention to provide materials and methods for improved adhesive bonding of composite and unfilled resins of the type polymerized by free radicals to dentin, enamel, industrial substrates, and/or other substrates containing or capable of binding metallic ions. The resulting products are also within the scope of the invention.

The invention comprises novel substrate-altering bonding agents, monomers, comonomers and polymerization initiators utilizing or containing divalent and/or polyvalent salts, bases, and/or cations for improving the value and effectiveness of polymeric adhesives and polymers in various applications. This invention is based upon the discovery that a hydrated, acidic, demineralized organic layer on the surface of cleansed or conditioned dentin constitutes a weak boundary layer which acts to limit the strength and durability of adhesive bonding mediated by the adhesive-promoting agents described in the prior art and above, unless di- or polyvalent cations are applied or resupplied to this interfacial region. This invention is believed to provide means (1) to supply this acid-rich demineralized surface layer or other substrates with divalent and/or polyvalent cations and/or polyamine compounds capable of: (a) bridging together, by a process herein termed "molecular ionic bridging", the unneutralized carboxyl, phosphate, and sulfate groups present in this demineralized layer, thereby hardening and strengthening this layer, (b) providing sites for binding the carboxyl or other groups of adhesion-promoting agents and monomers as described in the above-mentioned patents, and of those agents and monomers described in the co-pending patent application filed as "Hydrophilic Adhesive Monomers and Polymers Made Therefrom" (Ser. No. 07/791,999); and (c) promoting ionic bonding or "bridging" between carboxyl groups of these adhesive monomers and/or their polymers; (2) to raise the effective pH of this acidified hydrated layer to an effective pH close to physiological pH at which these structures are most stable; and (3) to provide a slight increase in radiopacity to aid in subsequent diagnostic evaluations. Utilizing the methods of this invention leads to more highly crosslinked polymers and improved interaction between adhesive bonding agents and polymers within the substrate, particularly dentin for preventive and conservative reparative dental applications, and provides for an unprecedented variety of potential uses in dental, medical and industrial applications, specifically where adhesive bonding is desired. The higher crosslink density resulting from the presence of divalent and/or polyvalent cations and/or polyamine compounds in the altered substrate-polymer structures imparts greater strength, durability, and dimensional stability while improving the storage stability of some of the ingredients and their solutions.

The effectiveness of the adhesive bonding agents found in the prior art depends on the interaction of their acidic functionalities with the calcified portion of dentin surfaces or with polyvalent cations bonded to other types of substrate surfaces. However, the organic portions of tooth enamel and dentin are themselves acidic in nature. The dentin matrix contains significant amounts of very acidic proteins, e.g., phosphophoryns comprised of about 45% phosphoserine and 35% aspartic acid residues; dentin sialoprotein, rich in aspartic and glutamic acid residues; osteocalcin; and others, in addition to collagen. Therefore, adhesive bonding agents comprised of acidic functionalities, or the monovalent inorganic salts thereof, cannot chemically react by ionic formation of salt bridges with the acidic, demineralized organic layer of surfaces that have been demineralized in the cleansing process. Di- or polyvalent cations must be resupplied to this interfacial region to overcome the resistance of this boundary layer to efficient adhesive bonding with such acidic adhesive agents.

A particular advantage of the present invention is that it supplies, along with adhesion-promoting agents, di- and polyvalent cations which can bring about molecular ionic bridging: (1) between the acidic (carboxyl, sulfate, phosphate or other) groups of substrate surfaces; (2) between these groups within the substrate and the acidic (carboxyl, phosphate or other) groups of the various adhesive-promoting agents (such as NTG-GMA and other compounds described more fully below); and (3) between the acidic (carboxyl or other) groups of the various adhesive resin monomers, such as PMDM and others including those described herein, in the prior art and in the co-pending application (Ser. No. 07/791,999), "Hydrophilic Adhesive Monomers and Polymers Made Therefrom", and their derivative polymers.

The present invention provides a method for achieving this improved molecular ionic bridging: by applying one or more of the adhesion-promoting agents in the form of salts or complexes of di- and polyvalent cations or polyfunctional compounds to surfaces to be adhesively bonded, such as dentin, enamel, or other natural or industrial substrates, more particularly to demineralized, acid-treated, or conditioned surfaces capable of binding such cations or compounds. The di- and polyvalent cations or complexes of the effective adhesion-promoting agents carry with them into this demineralized surface zone replacement ions for the natural divalent calcium cations or other cations that are removed in the cleansing process. Di- and polyvalent cations, most preferably, as well as di- and polyamines, preferably di- and polytertiary amines, have ionic bridging and linking characteristics not possessed by monovalent cations such as alkali metal elements (lithium, sodium, potassium, rubidium and cesium), known in the prior art (such as U.S. Pat. No. 4,964,911 and the above-referenced prior Bowen patents, especially U.S. Pat. No. 4,659,751, column 6, line 58). Importantly, the bonding strength of synthetic resins to such substrates depends on the strength and hardness of the interfacial regions, and this in turn is dependent upon the degree of linking, crosslinking and chain formation within the substrate material and the applied adhesive bonding agents.

Although it may be most preferable to have substantial stoichiometric equivalence, the divalent cations, polyvalent cations, amines, diamines, and polyamines may be present in a range between 20% of stoichiometric equivalence to the acidic or ligand groups of the adhesion-promoting agents and substantial excess such that the acidic or ligand groups of the adhesion-promoting agents are present at a level of as little as 1% of the stoichiometric equivalence to the divalent cations, polyvalent cations, amines, diamines, and polyamines.

Additionally, because most of the adhesive resin monomer molecules of this invention (such as PMDM and its analogues) have two or more carboxyl groups per molecule, di- and polyvalent cations or polyfunctional amines can increase the extent and concentration of crosslinking within this adhesive resin by salt-bridging in a chain-like manner, for example, by forming molecular ionic bonds between the positive charges on the di- and polyvalent cations and the negative charges on more than one of the carboxyl, phosphate, sulfate or other negatively-charged ligand groups on the adhesive monomers or within the substrate. This could induce a higher degree of crosslink density by adding ionic bonding, hydrogen-bonding, or charge-mediated bonding to the crosslinking otherwise brought about by the covalent bond-forming polymerization of the multiple vinyl methacrylate, acrylate, or other polymerizable groups of the monomer compounds such as PMDM and its analogues.

The less-effective monovalent alkali metal salts of such compounds known in the prior art (see, for example, U.S. Pat. No. 4,964,911, and particularly U.S. Pat. No. 4,659,751, column 6, line 58) cannot participate in this desirable molecular ionic bridging. In fact, monovalent alkali metal ions may disrupt this bridging. It is believed that none of the compositions described in U.S. Pat. No. 4,514,527, No. 4,521,550, No. 4,588,756, No. 4,659,751 and No. 4,964,911 can form molecular ionic bridging in the manner described in the present invention.

Surprisingly, an additional advantage of the novel di- and polyvalent salts or complexes of the effective compounds described herein is that they may be more soluble in optimal volatile, aprotic organic solvents (such as acetone), without the addition of water as a co-solvent, than the potentially less-effective monovalent alkali metal salts of such compounds known in the prior art (see, U.S. Pat. No. 4,964,911). The organic solubility of these newly discovered di- and polyvalent cation salts and complexes of the adhesion-promoting agents makes possible a significant improvement in adhesive bond strengths and the durability of the resulting structures.

It is an additional advantage of the present invention that the novel di- and polyvalent salts or complexes of the effective adhesion-promoting agents described herein are easily prepared and render the active ingredients more stable than NTG-GMA against degradation during formulation and storage before use.

It is a further advantage of this invention that the materials and procedures provided by the invention are within acceptable ranges of cost, manufacturing feasibility, storage stability, and operational intricacy to the user.

Thus, in a first aspect the present invention provides a method for adhesively bonding resins or composite materials to tooth or other tissues, or industrial or natural substrates containing or capable of binding di- or polyvalent cations or amines, which method comprises contacting the surface with an aqueous solution comprising at least one acid, acidic salt, or chelating or sequestering agent; contacting the surface with a solution comprising a solvent and at least one adhesion-promoting agent selected from the group consisting of N-phenylglycine (NPG) and derivatives and analogues thereof [for example: the addition reaction product of N(p-tolyl)glycine and glycidyl methacrylate (NTG-GMA); the adduct of N-phenylglycine and glycidyl methacrylate (NPG-GMA); the adduct of N(4-chlorophenyl)glycine and glycidyl methacrylate (NCPG-GMA); the adduct of N-phenylglycine and 1,2-epoxy-3-phenoxypropane (NPG-PGE); the adduct of N-phenylglycine and p-chlorophenyl-2,3-epoxypropyl ether (NPG-CGE); the adduct of N-p-chlorophenylglycine and p-chlorophenyl-2,3-epoxypropyl ether (NCG-CGE); the reaction product of N-p-chlorophenylglycine and phenyl-2,3-epoxypropyl ether (NCG-PGE); the adduct of N-phenylalanine and glycidyl methacrylate (NPA-GMA); and the GMA (glycidyl methacrylate) adduct of N-tolyl-2 (or alpha)-alanine (NTA-GMA); N-phenylalanine; 2-(N-phenyl) alkanoic acids and their glycidyl methacrylate adducts], and other amino acids, in the form of salts and complexes of these compounds with at least one member of the group consisting of di- and polyvalent cations, and salts of diamines or polyamines, wherein the di- and polyvalent cations are preferably selected from the group consisting of alkaline earth elements (magnesium, calcium, strontium, barium), iron, aluminum, zinc, chromium, manganese, cobalt, copper, and molybdenum, wherein the di- and polyvalent salts and complexes for each mixture comprise between 1 and 100% of the total mixture; and contacting with the surface a liquid comprising at least one adhesive resin monomer selected from the group consisting of (1) reaction products of dianhydrides with molecules containing at least one methacrylate, acrylate or other polymerizable group and also one reactive hydroxyl group, or primary or secondary amino group, (2) 4-methacryloxyethyltrimelliticanhydride and its dicarboxylic acid hydrolysis derivative, (3) other compounds containing at least one group or moiety capable of free radical polymerization and at least one aromatic ring or moiety containing electron-withdrawing substituents that do not interfere with free radical polymerization, and (4) other compounds containing at least one group or moiety capable of free radical polymerization and at least one carboxyl group or salt thereof, optionally in the presence of a solvent, wherein the solvent comprises between 0 and 99.9% of the liquid.

In another embodiment of the invention, a sulfinic acid, a derivative of a sulfinic acid, a salt of a sulfinic acid, such as sodium or lithium p-toluene sulfinate, or, preferably, a di- or polyvalent salt or mixture of salts of a sulfinic acid may be used as a polymerization initiator preceding or in conjunction with one or more of the foregoing materials or application steps. Other polymerization initiators, photoinitiators or co-photoinitiators may optionally be combined with the foregoing components. Such polymerization photoinitiators or co-photoinitiators include camphorquinone or derivatives of camphorquinone; amines, preferably tertiary amines having a hydrogen atom attached to a carbon atom adjacent to a nitrogen atom; and benzoyl or other peroxides.

Combinations of all, or various components may be mixed together before application to surfaces to be bonded. Polymerization initiators, accelerators, photoinitiators, and/or cophotoinitiators; acids, acidic salts, chelating and/or sequestering agents; adhesion-promoting agents; adhesive monomers; and polymerizable resins and/or composites may be mixed together before application to surfaces to be bonded in various combinations and orders of application, in which appropriate and effective combinations and permutations are known by those skilled in the art.

In using these methods provided by the invention, it is preferred that the steps be performed in the order specified above. Preferred acids, acidic salts, chelating or sequestering agents include but are not limited to nitric acid, phosphoric acid, formic acid, maleic acid, hydrochloric acid, a sulfinic acid, pyruvic acid, and other acids, ethylenediaminetetraacetic acid (EDTA), their soluble salts, and mixtures and buffered solutions thereof. The preferred adhesion-promoting agents useful in performing the methods of this invention include N-arylglycine and N-arylalanine derivatives and ring-substituted N-arylglycine and N-arylalanine derivatives, wherein the derivatives contain at least one free carboxyl group and at least one polymerizable group, such as a methacrylate, acrylate, vinyl or other group capable of free radical polymerization. The most preferred adhesion-promoting agents are the di- and polyvalent element cationic complexes of the addition reaction product of: N(p-tolyl)glycine and glycidyl methacrylate (NTG-GMA); the adduct of N-phenylglycine and glycidyl methacrylate (NPG-GMA); the adduct of N(4-chlorophenyl)glycine and glycidyl methacrylate (NCPG-GMA); the adduct of N-phenylalanine and glycidyl methacrylate (NPA-GMA); and the adduct of N(p-tolyl)alanine and glycidyl methacrylate (NTA-GMA).

Preferred adhesive resin monomers include the reaction products prepared from molecules containing at least one methacrylate, acrylate or other polymerizable group and also one reactive hydroxyl group, or primary or secondary amino group, reacted with classes of reactants, one class of which is dianhydrides selected from one or more of the group consisting of 5-[2,5-dioxotetrahydro-3-furanyl]-3-cyclohexene-1,2-dicarboxylic anhydride, symmetrical biphenyl tetracarboxylic dianhydride, glycerol acetate bistrimellitate dianhydride, polyol trimellitate dianhydride, 3,3',4,4'-diphenylsulfone tetracarboxylic dianhydride, 4,4'-oxydiphthalic anhydride, 4,4'-hexafluoroisopropylidene-bisphthalic anhydride, pyromellitic dianhydride, 3,3',4,4'-benzophenone tetracarboxylic dianhydride, ethylene glycol bistrimellitate dianhydride, mellophanic dianhydride, bicyclo[2.2.2]octane-2,3,5,6-tetracarboxylic dianhydride, bicyclo[2.2.2]-7-octene-2,3,5,6-tetracarboxylic dianhydride, and 1,2,3,4-cyclopentanetetracarboxylic dianhydride. Most preferred adhesive monomer agents include (1) the addition reaction product of pyromellitic acid dianhydride and glyceroldimethacrylate, (2) the addition reaction product of 3,3',4,4'-benzophenonetetracarboxylic dianhydride and glyceroldimethacrylate and (3) 4-methacryloxyethyltrimellitic anhydride. However, other compounds containing at least one group or moiety capable of free radical polymerization and at least one carboxyl group or salt thereof may be used; for example, the acidic forms or divalent or polyvalent salts of the reaction products of succinic anhydride and/or other monoanhydrides with molecules containing at least one methacrylate, acrylate or other polymerizable group and also one reactive hydroxyl group, or primary or secondary amino group, because of the molecular ionic bridging provided within the scope of this invention.

The components utilized in each step of the methods of this invention are preferably in solution dissolved in one or more solvents. Preferred solvents include compatible organic water-miscible solvents sufficient to carry the compound or compounds and the salts and complexes thereof into intimate contact with and/or to infiltrate hydrated or hydrophobic substances. The most preferred organic solvent is acetone.

Additional components useful in the practice of certain embodiments of the methods of this invention include: (1) trace amounts of divalent and polyvalent metal cations other than those specified above; (2) polymerization initiator compounds comprising divalent and polyvalent salts of toluene-4-sulfinic acid, aromatic sulfinic acids, sulfinic acid derivatives, sulfinic acids, or other sulfinate salts; and (3) other adhesion-promoting agents and di- and polyvalent cationic salts and complexes therein, most preferably N-phenylglycine, N-methyl-N-phenylglycine and N(p-tolyl)glycine and mixtures thereof.

The presence of minor or trace amounts of the acidic (zwitterionic) form and/or monovalent (alkali element) salts admixed with di- and polyvalent salts and complexes of the adhesion-promoting agents falls within the scope of this invention; however, the inclusion of acidic (zwitterionic) forms and/or monovalent (alkali element) salts is considered undesirable to the extent that they decrease storage stability and capacity for promoting molecular ionic bridging within the bonded interface.

Ammonium salts ($NH_{4+}$) and quaternary ammonium salts of the adhesion-promoting agents are contemplated as a means to alter, adjust, or neutralize the effective pH of these compounds and possibly stabilize them during storage; these salts may be admixed with diamine and/or polyamine salts and/or the more preferred di- and/or polyvalent cation salts or complexes of the adhesion-promoting agents. The ammonium salts lack the capability of molecular ionic bridging, and to the extent that such compounds interfere with molecular ionic bridging, they are not preferred. However, such ammonium salts and quaternary ammonium salts of adhesion-promoting agents may participate in hydrogen-bond bridging and to this extent they are desirable. Such compounds may also have other desirable qualities, such as the possibility of antimicrobial activity in the case of certain quaternary or other ammonium salts of adhesion-promoting agents, such as, for example, benzalkonium salts, cetylpyridinium salts, chlorhexidine salts, and other antimicrobial compound salts of an adhesion-promoting agent. Other antimicrobial compounds might be incorporated, with beneficial effects, into one or more of the compositions of this adhesive bonding system. In addition, ammonium salts or complexes might also improve the solubility of salts or complexes of adhesion-promoting agents with certain di- or polyvalent cations.

A second aspect of this invention provides an article of manufacture comprising in combination: (a) a first container containing a composition comprising at least one acid, acidic salt, or chelating or sequestering agent; (b) a second container containing a composition comprising at least one adhesion-promoting agent selected from the group consisting of N-phenylglycine (NPG) and derivatives and analogues thereof, N(p-tolyl)glycine (NTG) and derivatives and analogues thereof and other amino acids in the form of salts and complexes of these compounds with at least one member of the group consisting of di- or polyvalent cations, and salts of diamines or polyamines, wherein the divalent and polyvalent cations are preferably selected from the group consisting of cations of alkaline earth elements (magnesium, calcium, strontium, barium), iron, aluminum, zinc, chromium, manganese, cobalt, copper, and molybdenum, wherein the divalent and polyvalent salts and complexes for each mixture preferably comprise between 1 and 100% of the total mixture, and (c) a third container containing a composition comprising at least one adhesive resin monomer selected from the group consisting of (1) reaction products of dianhydrides with molecules containing at least one methacrylate, acrylate or other polymerizable group and also one reactive hydroxyl group, or primary or secondary amino group, (2) 4-methacryloxyethyltrimelliticanhydride and its dicarboxylic acid hydrolysis derivative, (3) other compounds containing at least one group or moiety capable of free radical polymerization and at least one aromatic ring or moiety containing electron-withdrawing substituents that do not interfere with free radical polymerization; and (4) other compounds containing at least one group or moiety capable of free radical polymerization and at least one carboxyl group or salt thereof. These may optionally be in the presence of a solvent, wherein the solvent comprises between 0 and 99.9% of the liquid. The first, second and third containers may be packaged together in the article of manufacture.

In an alternative embodiment, the article of manufacture includes one or more additional containers containing one or more compositions comprising at least one compound selected from the group consisting of a salt of a sulfinic acid, such as sodium or lithium p-toluene sulfinate or, preferably, a di- or polyvalent salt or mixture of salts of a sulfinic acid, and/or camphorquinone or a derivative of camphorquinone.

In a preferred embodiment, the contents of each of the containers is in a solution comprised of each component and a solvent, wherein the solvent comprises between 0 and 99.9% of each solution.

It is a particular advantage of the present invention that the di- and polyvalent salts and complexes of the adhesion-promoting agents provided by the invention are soluble in organic solvents. Moreover, the novel di- and polyvalent salts or complexes of the effective adhesion-promoting agents described herein are readily prepared by admixture of their component, preferably aqueous, solutions from which they rapidly precipitate, facilitating their isolation and purification. In addition, preparation of these agents in this way renders the active ingredients more stable against degradation during formulation and storage before use.

Thus, an additional aspect of the present invention provides a method for preparing the divalent and polyvalent salts and complexes of adhesion-promoting agents of the invention comprised of (a) providing a first, preferably aqueous, solution comprised of monovalent cationic salts or ammonium or amine salts or an acidic or a zwitterionic form of at least one adhesion-promoting agent selected from the group consisting of N-phenylglycine (NPG), and derivatives and analogues thereof, and other amino acids; (b) providing a second concentrated solution of at least one di- or polyvalent cationic salt wherein the cation of the salt is preferably selected from the group consisting of alkaline earth elements (magnesium, calcium, strontium, barium), iron, aluminum, zinc, chromium, manganese, cobalt, copper, and molybdenum; (c) mixing said first and second solutions by stirring to form a precipitate of divalent or polyvalent salts and complexes thereof; (d) separating the precipitate from the solution; (e) optionally washing the precipitate with water; and (f) optionally drying the precipitate in the presence of oxygen and stabilizers if polymerizable groups are present. In a preferred embodiment, the first solution comprises an aqueous solution optionally comprised of at least one water-miscible solvent, most preferably acetone. The divalent or polyvalent salt of the second concentrated solution is most preferably magnesium chloride, calcium nitrate, calcium chloride or aluminum nitrate. In the most preferred embodiment of the invention, each of the first solution of subpart (a), the second solution of subpart (b) and the composition of subpart (c) also contains at least one polymerization inhibitor selected from the group consisting of 4-hydroxymethyl-2,6-di-tert-butylphenol, 2,5-di-tert-butyl hydroquinone, tert-butyl hydroquinone, 4-hydroxy-3,5-di-tert-butylphenyl propionic acid, 3,3'-thiodipropionic acid, 3,5-di-t-butyl-4-hydroxyanisole, the monomethyl ether of hydroquinone, and hydroquinone.

Preferred di- and polyvalent salts and complexes of adhesion-promoting agents provided by this invention include those of N-phenylglycine; N-tolyl-alpha-alanine; N-phenylalanine (NPA), its derivatives and analogues, which incude, for example, N-methyl-N-phenylalanine, NTA-GMA, and others; N-methyl-N-phenylglycine; N(p-tolyl)glycine; the adduct of N-phenylglycine and glycidyl methacrylate (NPG-GMA) and the addition reaction product of N(p-tolyl)glycine and glycidyl methacrylate (NTG-GMA).

Specific preferred embodiments of the present invention will become evident from the following more detailed description of certain preferred embodiments and the claims.

DETAILED DESCRIPTION OF PREFERRED EMBODIMENTS

This invention comprises materials and methods for improving the adhesion of composite materials to dentin and enamel. The invention also comprises the resultant products. The terms "composite material" and "composite resin" are used herein to refer to materials which can polymerize or harden by free radical mechanisms. "Resins" refers to monomers (or their polymers) without significant filler content. Typical examples include methacrylates, acrylates and polyesters.

In the practice of this invention, following the cleansing or modification of the substrate surface and removal or modification of substantially all of the dissolved debris, preferably by the use of a solution comprising at least one acid, acidic salt, or chelating or sequestering agent in a concentration between about 0.1% and 50%, most preferably in a concentration that is approximately isotonic with physiologic saline solution, and after substantially removing the derivative solution from the surface, an organic solution containing one or more of the di- or polyvalent cation complexes of adhesion-promoting agents (e.g., NTG-GMA or its analogues), preferably contained in a water-miscible solvent, such as acetone, is applied to the treated substrate surface. A solution of an effective adhesive resin monomer (e.g., PMDM or its analogues) is then applied to the substrate surface and excess solvent removed by evaporation.

Alternatively, the solution of the di- or polyvalent cation complexes or salts of the adhesion-promoting agents (such as NTG-GMA and/or its analogues) is mixed with a solution of the adhesive resin monomers (such as PMDM and/or its analogues), and this mixture is immediately applied to the cleansed substrate surface to be bonded, after which excess solvent is removed by evaporation.

It is further contemplated that mixtures comprising the acidic or chelate-mediated cleansing solution, a solution of the di- or polyvalent cation complexes or salts of the adhesion-promoting agents (such as NTG-GMA and/or its analogues), and a solution of the adhesive resin monomers (such as PMDM and/or its analogues), and (optionally) added polymerization initiators, could be prepared before being applied to the substrate surface to be bonded, after which excess solvent is removed by evaporation. Such mixtures are prepared immediately before application for combinations of compositions containing amines and peroxides, NPG or its derivatives or analogues and PMDM or its derivatives or analogues, and/or sulfinic acids or their salts or derivatives and, optionally, acidic compounds.

Additional copolymerizable monomers and/or composite materials and/or other substances can then be applied as desired and substances to be bonded can then be placed in contact with the prepared surface for adhesive bonding.

When an acid comprises the first cleansing treatment solution, it renders the solution low in pH. The most preferred acid for use in the inventive method is nitric acid, ranging in concentration from 0 to 50% by weight, preferably 0.068 to 10% by weight and most preferably of a concentration of about 2.5% by weight of the aqueous solution. Acids other than nitric, for example, phosphoric, hydrochloric, sulfuric, formic, maleic, pyruvic, sulfinic, and other acids, may similarly be effective in improving the bond strengths obtainable in the use of the present invention.

In addition, such a cleansing solution can comprise a chelating agent, such as ethylenediaminetetraacetic acid (EDTA), and others, including their soluble salts, and mixtures and buffered solutions thereof may be used.

As the next step in the most preferred inventive method, a solution of di- and polyvalent cation salts or complexes of the effective adhesion-promoting agents (such as NPG, NTG, NPG-GMA or, most preferably, NTG-GMA or NTA-GMA) in a volatile, water-miscible solvent is applied to the surface of the dentin or enamel or other substrate.

NPG is available commercially. It can be synthesized by the route of Example 1b of U.S. Pat. No. 4,588,756, with the exception that analine is substituted for p-toluidine. NTG-GMA is the adduct of N(p-tolyl)glycine and glycidyl methacrylate. NTG-GMA may be synthesized readily from commercially available compounds by the route of Example 1b of U.S. Pat. No. 4,588,756.

A number of di- and polyvalent salts of NTG and NTG-GMA are prepared as follows. Para-toluidine (2.43 mols) is reacted with monochloroacetic acid (2.00 mols) in the presence of a stoichiometric or other appropriate amount of a cationic carbonate or hydroxide in a methanol-water solution at reflux (about 80° C.) for about 5 hours. The methanol is then boiled off, and the NTG is precipitated on cooling from the resulting aqueous solution. The excess p-toluidine is removed by extraction with ether, and the NTG salt recrystallized.

The NTG salt in mixed solvents, stabilized with hydroquinone and di-tert-butyl sulfide, is reacted with a methanolic solution of glycidyl methacrylate (GMA) at 23° C., the latter solution added dropwise, with stirring. The salt of NTG-GMA precipitates upon removal of the organic components of the solvent mixture.

Di- and polyvalent cation salts and complexes of such adhesion-promoting agents are readily and economically prepared by the admixture (with stirring) of solutions of a salt, such as a salt with a monovalent cation or an amine or ammonium compound, of an acid or a zwitterionic form of at least one adhesion-promoting agent selected from the group consisting of NPG, NTG, NPG-GMA, NTG-GMA, NTA-GMA and/or their analogues, and/or other amino acids, with a concentrated solution of at least one di- or polyvalent cation salt or amine or polyamine compound. Preferred di- and polyvalent salts include magnesium chloride, calcium acetate, and aluminum nitrate, and soluble salts of strontium and zinc. Preferred polyamine compounds include, but are not limited to, the soluble salts of 1,4-diazabicyclo[2.2.2] octane and hexamethylene tetramine. The adhesion-promoting agents are preferably in solution with an appropriate water-miscible solvent and/or water in combination (for example, 50/50 ethanol-water solution); the concentrated di- and polyvalent cationic salt solutions are preferably aqueous solutions. These solutions also preferably contain one or more soluble polymerization inhibitors such as hydroquinone or other polymerization inhibitors or stabilizing antioxidants well known to those skilled in the art. Admixture of these solutions promptly leads to the precipitation of the relatively water-insoluble di- and polyvalent cation salts and complexes of the adhesion-promoting agents. These precipitates are then washed with water, preferably containing trace amounts of hydroquinone or other appropriate inhibitors, and the precipitates dried and separated by filtration, maintaining the presence of oxygen and traces of said inhibitors to prevent premature polymerization of polymerizable groups. Such dried di- and polyvalent cationic salts and complexes of adhesion-promoting agents can be stored or put into solution in acetone, other solvents or mixtures of solvents, if desired.

Alternatively, these adhesion-promoting agents may be initially synthesized in the presence of and with the aid of di- or polyvalent cation compounds to directly form the desired products. For example, a method for preparing the di- and polyvalent salts and complexes of adhesion-promoting agents comprises: condensing divalent or polyvalent cation salts of haloacetic acids or 2-halopropanoic or other 2-haloalkanoic acids with amino acids selected from the group consisting of analine ring-substituted derivatives and analogues of analine (such as for example, toluidines, xylidines, trimethylanilines) and other amines, which salts do not undergo adverse interactions or form totally insoluble reaction products, optionally reacting said reaction products with compounds containing alkylating moieties and polymerizable groups, and separating the precipitated divalent and polyvalent salts and complexes of adhesion-promoting agents from the solution. As a specific example, calcium chloroacetate or calcium-2-bromopropionate could be condensed with two moles of p-toluidine in the presence of at least one mole of calcium carbonate, and the resulting intermediate reacted with two moles of glycidyl methacrylate (GMA) to yield directly the calcium salt or complex of NTG-GMA or NTA-GMA, respectively.

The di- and polyvalent salts and complexes of the adhesion-promoting agents contemplated in the present invention include those of calcium, aluminum, magnesium, strontium and zinc cations, as most preferred, and barium, iron, chromium, manganese, cobalt, copper, and molybdenum, and other transition metallic elements, as well as any other of the di- or polyvalent cations in the periodic table (with the exception of those transition metals that undergo adverse interactions and those cations that form totally insoluble reaction products), amines, and mixtures of these salts and complexes.

Effective adhesion-promoting agents that comprise the di- and polyvalent salts and complexes of the present invention include those of N-phenylglycine (NPG) and the derivatives and analogues of NPG, which include but are not limited to the addition reaction product of N(p-tolyl)glycine and glycidyl methacrylate (NTG-GMA); the adduct of N-phenylglycine and glycidyl methacrylate (NPG-GMA); N(p-tolyl)glycine (NTG); N-methyl-p-tolylglycine; N(4-chlorophenyl)glycine (NCPG); the adduct of N(4-chlorophenyl)glycine and glycidyl methacrylate (NCPG-GMA); the adduct of N-phenylglycine and 1,2-epoxy-3-phenoxypropane (NPG-PGE); the adduct of N-phenylglycine and p-chlorophenyl-2,3-epoxypropyl ether (NPG-CGE); the adduct of N-p-chlorophenylglycine and p-chlorophenyl-2,3-epoxypropyl ether (NCG-CGE); the reaction product of N-p-chlorophenylglycine and phenyl-2,3-epoxypropyl ether (NCG-PGE); N-methyl-N-phenylglycine (NMNPG); N-methyl-N-phenylalanine (NMNPA); N-methyl-N(p-tolyl)alanine (NMNPTA); the adduct of N-phenylalanine and glycidyl methacrylate (NPA-GMA); the adduct of N(p-tolyl)alanine and glycidyl methacrylate (NTA-GMA); and other N-arylglycine and N-arylalanine derivatives, including ring-substituted N-arylglycine and N-arylalanine derivatives, said derivatives preferably containing at least one free carboxyl group, and most preferably containing at least one polymerizable group exemplified by vinyl groups including methacrylate and acrylate groups.

Alternatively, mixtures of N-phenylglycine (NPG) and the derivatives and analogues of NPG, in the form of preferably aqueous solutions of their monovalent salts, can be mixed with preferably aqueous solutions of at least one di- or polyvalent cation salt or polyamine compound to form precipitates, useful in the present invention because of facilitated solubility in organic solvents, monomers, and components described herein.

A solution of one or more di- and polyvalent cation salts or complexes of an effective adhesion-promoting agent (such as NPG, NTG, NTA, NPG-GMA, NTG-GMA or NTA-GMA) is applied to dentin and enamel surfaces dissolved in a volatile water-miscible solvent. In this context, the term "solvent" is intended to include solvent mixtures. The preferred solvent is acetone, which is volatile, relatively innocuous and miscible with water (thereby allowing relatively water-insoluble solutes like di- and polyvalent cation salts or complexes of NPG, NTG, NPG-GMA or NTG-GMA to infiltrate substrate surface sites); acetone may also have other advantageous characteristics. A 5% solution of the di- or polyvalent cation salts or complexes of the effective adhesion-promoting agent in acetone is efficacious. Other concentrations, preferably within the range of about 0.1% to a saturated solution, and other solvents, singly and as mixtures, may be employed. Less-preferred solvents include ethanol, methanol, and volatile esters. Isopropyl alcohol (2-propanol) is not recommended as a solvent because it resulted in tooth-to-resin bond strengths less than one-half those achieved when acetone was used.

After the solution of di- and polyvalent cation salts or complexes of the effective adhesion-promoting agents (such as NPG, NTG, NPG-GMA, NTA-GMA or NTG-GMA) has remained in place preferably about 5 to about 90 seconds, 60 seconds being most preferred, excess solvent is removed if the solution has not evaporated to dryness, and the tooth surface is then dried, generally with air.

As the next step in the most preferred inventive method, a liquid comprising at least one adhesive resin monomer selected from the group consisting of (1) reaction products of dianhydrides with molecules containing at least one methacrylate, acrylate or other polymerizable group and also one reactive hydroxyl group, or primary or secondary amino group, (2) 4-methacryloxyethyltrimelliticanhydride and its dicarboxylic acid hydrolysis derivative, and (3) other compounds containing at least one group or moiety capable of free radical polymerization and at least one aromatic ring or moiety containing electron-withdrawing substituents that do not interfere with free radical polymerization, in the same or a different volatile solvent(s), is applied to the surface of the dentin or enamel. Preferably this monomer solution is comprised of at least one of the following: (1) the addition reaction product of pyromellitic acid dianhydride and glyceroldimethacrylate (PMGDM); (2) the addition reaction product of 3,3',4,4'-benzophenonetetracarboxylic dianhydride and glyceroldimethacrylate (BTD A-GDM); (3) PMDM, synthesized in essentially the same way as described in U.S. Pat. No. 4,588,756; (4) BTDA-HEMA, the addition reaction product of 3,3',4,4'-benzophenonetetracarboxylic dianhydride and 2-hydroxyethyl methacrylate; (4) adhesive resin monomeric compounds disclosed in U.S. patent application Ser. No. 07/791,999, filed Nov. 14, 1991; and/or (5) trimellitic anhydride dimethacrylate, which is the reaction product of trimellitic anhydride acid chloride and glyceroldimethacrylate. BTDA-HEMA may be synthesized by a set of procedures analogous to those used to synthesize PMDM, wherein 3,3',4,4'-benzophenone tetracarboxylic dianhydride is substituted in place of the pyromellitic acid dianhydride.

The exact chemical structures of some of the aforesaid compounds are not definitely known, and are best characterized as the above-recited addition reaction products.

PMGDM was synthesized as follows. One mole of pyromellitic acid dianhydride was heated together with about 2 moles of glyceroldimethacrylate in a volatile, anhydrous, aprotic solvent in the presence of a tertiary amine and a small amount of BHT (butylated hydroxy toluene), an antioxidant and polymerization inhibitor or stabilizer. The dry acetone solvent was removed by evaporation, leaving a clear, nearly colorless liquid product, PMGDM.

These and/or other adhesive resin monomeric compounds disclosed in U.S. patent application Ser. No. 07/791,999, filed Nov. 14, 1991 may be applied to the dentin or enamel surface in any desired proportions, dissolved in a solvent or a mixture of solvents. Again, the preferred solvent is acetone, although other solvents may be used. A 10% solution of PMDM in acetone is efficacious, although other concentrations, preferably in the range of about 0.1% to a saturated solution, may be used.

After application to a surface prepared as described hereinabove, the excess solution of PMDM and/or other adhesive resin monomer preferably is not removed, but rather, the solvent is removed by evaporation that may be speeded by applying a gentle stream of air at any feasible temperature.

After the dentin or enamel surface is prepared as described above, a mix of composite or unfilled resin may be applied and the adhesive bond strength of the resulting bonded material tested. The testing method was essentially the same as that described in Bowen R. L., "Adhesive Bonding of Various Materials to Hard Tooth Tissues. I. Method of Determining Bond Strength", J. Dent. Res. 44:690–695 (1965). Briefly, a mix of a composite resin (for example Adaptic* Dental Restorative, available from Johnson & Johnson, East Windsor, N.J.; Concise* from 3M Co., St. Paul, Minn.; or others from other companies) was made, applied to the opposing plunger part of a test assembly, slowly let down onto the dentin surface, and weighted with a pressure of about 1.0 MPa (150 psi) for 5 seconds to spread the composite on the dentin surface. (The pressure during the resin application to the dentin was somewhat less than 1.0 MPa because the tapered part of the iris supported some of the load.) The assembly was let stand in air for 15 minutes, then immersed in distilled water at room temperature until tested 1–10 days later. Many bonds to dentin or enamel of extracted teeth have required over one ton (2,000 lbs.) per square inch to break in tension, with fractures occurring occasionally within the dentin itself and frequently in the composite material, as well as at regions in between these two materials.

For use in dentistry and other applications where aesthetics is important, the most preferred di- and polyvalent cations are magnesium, calcium, zinc, aluminum and strontium. Barium ions can also be used where its possible toxicity is not a detriment. For industrial and other applications, any of the di- or polyvalent cations in the periodic table can be used in like manner, with the exception of those transition metals that undergo adverse interactions with compounds of this type and those cations that form insoluble reaction products. For example, ferric or ferrous ions will form a brown complex with NPG, but if excess ferric ions are present, the complex decomposes under normal conditions; at present it is not known if this composition requires the presence of oxygen. However, the stoichiometric combination of ferric ions and NPG forms an apparently stable brown complex, as do complexes formed with a slight excess of three NPG molecules per ferric ion. The use of high concentrations of such ferric-, ferrous-, or other iron-containing complexes in dental applications is not recommended where aesthetics is important to avoid the occasional formation of staining or marginal discoloration; whereas low, optimal concentrations may beneficially improve polymerization initiation and bond strengths without causing discoloration. Toxic levels of other di- or polyvalent cations are also excluded, but adequately low concentrations of nutritionally desirable "trace elements", including but not limited to chromium, manganese, cobalt, copper, molybdenum, and zinc, in appropriate valence states are included within the scope of this invention. Amine salts of adhesion-promoting agents (such as NTG-GMA), preferably tertiary amines, including "Dabco" (1,4diazabicyclo[2.2.2]octane), and most preferably relatively nontoxic, di- or polytertiary amines, such as and including hexamethylenetetramine (methenamine), and others, fall within the scope of this invention.

Water-miscible solvent solutions of di- and polyvalent salts and complexes of effective adhesion-promoting agents (such as NPG, NTG, NPG-GMA, NTG-GMA, NTA-GMA, NPG, derivatives or analogues thereof, and/or other amines or amino acids, preferably aromatic amino acids), can also be applied to treated substrate surfaces in the form of amine salts, preferably salts of diamines or polyamines, and most preferably wherein the amines, diamines, or polyamines comprise compounds containing predominately or exclusively tertiary amino groups to accomplish the same purpose of penetrating the hydrophilic surface layers and initiating or helping to initiate polymerization of effective monomer adhesive agents, such as PMDM, its analogues, and/or other monomers, to improve adhesive bonding. One or more amines for forming such salts and complexes can include $NH_3$, primary, secondary, and tertiary amines, ammonium and quaternary ammonium compounds, where polyfunctionality is preferred. Examples of tertiary amines include hexamethylenetetramine, 1,4-diazabicyclo[2.2.2]octane, quinuclidine, N,N-diethylethanolamine, N-ethyldiethanolamine, triethanolamine, N,N-dihydroxy-p-toluidine, 3-quinuclidinol, N,N-dihydroxyethylglycine, N,N-dimethylglycine, 2-quinuclidine carboxylic acid, N,N-dimethylaminoethylmethacrylate, and N,N-diethylaminoethylmethacrylate.

Specific polymerization inhibitors, antioxidants, or stabilizers must be used in very small concentrations, typically 0.001 to 1% by weight of the overall formulation, during the syntheses and storage of polymerizable compounds of the present invention. Illustrative examples include 4-hydroxymethyl-2,6-di-tert-butylphenol;2,5-di-tert-butylhydroquinone,tert-butylhydroquinone, 4-hydroxy-3,5-di-tert-butylphenyl propionic acid, 3,3'-thiodipropionic acid, 3,5-di-tert-butyl-4-hydroxyanisole, BHT, the monomethyl ether of hydroquinone, and hydroquinone.

Advantageously, the components necessary to effect the method of this invention may be packaged in an article of manufacture or "kit" for use by dentists or others. As an illustration for the most preferred embodiment of the invention, such an article of manufacture would comprise one or more of each of the following: (a) a first closed compartment that is preferably impervious to ultra-violet and to blue light or to all light (e.g., an amber glass bottle, a plastic, sealable container, a capsule or compartment within a capsule, or other device) containing a composition comprising at least one acid (preferably nitric acid), acidic salt, or chelating or sequestering agent (and which may additionally contain other additives); (b) a second closed compartment that is also preferably impervious to ultraviolet and to blue light or to all light, (e.g., an amber glass bottle, a plastic, sealable container, a capsule or compartment within a capsule, or other device) containing a composition comprising at least one adhesion-promoting agent selected from the group consisting of N-phenylglycine (NPG) and derivatives and analogues thereof, and other amino acids in the form of salts and complexes of these compounds with at least one species of divalent or polyvalent cation, or amine salt, preferably salts of diamines or polyamines, and most preferably wherein the amines, diamines, or polyamines comprise compounds containing predominately or exclusively tertiary amino groups, and/or members selected from the group consisting of ammonium salts, quaternary ammonium salts, diamine salts, polyamine salts, chlorhexidine salt, alexidine salt, benzalkonium salt, cetylpyridinium salt, and other antimicrobial compounds, preferably as salts of adhesion-promoting agents, and wherein the divalent and polyvalent cations are selected from the group consisting of alkaline earth elements (magnesium, calcium, strontium, barium), iron, aluminum, zinc, chromium, manganese, cobalt, copper, and molybdenum, wherein these salts and other active components comprise between 1 and 100% of the total mixture; and (c) a third closed compartment that is preferably impervious to UV or visible light containing a composition comprising at least one monomer selected from the group consisting of (1) reaction products of dianhydrides with molecules containing at least one methacrylate, acrylate or other polymerizable group and also one reactive hydroxyl group, or primary or secondary amino group, (2) 4-methacryloxyethyl-trimelliticanhydride and its dicarboxylic acid hydrolysis derivative, and (3) other compounds containing at least one group or moiety capable of free-radical polymerization and at least one aromatic ring or moiety containing electron-withdrawing substituents that do not interfere with free radical polymerization.

Optionally, such an article of manufacture would include (d) a fourth closed compartment containing a salt of a sulfinic acid (for example, sodium or lithium p-toluene sulfinate) or, preferably, a di- or polyvalent salt or mixture of salts of a sulfinic acid to be used as a polymerization initiator immediately preceding or in conjunction with one or more of the foregoing materials or application steps.

Optionally, such an article of manufacture would also include (e) a closed compartment containing camphorquinone or a derivative of camphorquinone as a photoinitiator of polymerization that may optionally be combined with at least one of the foregoing components.

One or more of the components, namely, the acidic or chelating components of compartment (a), the adhesion-promoting agents of compartment (b), the adhesive resin monomers of compartment (c), the polymerization initiators of compartment (d), and the photoinitiators of compartment (e), may optionally be mixed together immediately before application to the surface(s) to be bonded. One example of means to accomplish this is the use of capsules having breachable membranes to separate compartments containing the desired components; such membranes can be ruptured and components mixed by pressure-applying devices and/or vigorous agitation of the capsules. Such technology is well known in the arts to which this invention applies.

The acidic or chelating components of compartment (a), the adhesion-promoting agents of compartment (b), the adhesive resin monomers of compartment (c), the polymerization initiators of compartment (d), and the photoinitiators of compartment (e) may be included in the kit in solution form or in a form which would facilitate preparation of solutions.

It is believed that bonding using the methods of this invention may be improved especially (when utilizing resins, surface coatings, monomers, prepolymers, or plastics that harden by free radical reactions, and especially those bonded systems that are subsequently exposed to water or moisture) to industrial substrates which include or comprise various kinds of wood, wood products, cellulosic fibers, films and materials having vicinal oxygen substituents on adjacent carbon atoms on accessible surfaces; metals, metal alloys, metal compounds, and metal composites having oxide or hydroxide surface groups containing or capable of binding the metallic cations listed above; glasses, microcrystalline glasses, ceramics, porcelains, natural and artificial minerals (both crystalline and amorphous), and inorganic solids having oxide or hydroxide surface groups; calcified, decalcified, and noncalcified surfaces such as bone, ivory, horn, leather, and other collagenous, keratinous and proteinaceous substances; and other solid materials, both natural and artificial, providing that they have vicinal or sufficient oxygen, nitrogen or sulfur ligands to bind metallic cations on their surfaces. In general, any substrate containing or capable of binding metallic ions is a candidate for enhancement of adhesive bonding by the methods of the present invention.

Adhesive bonding of resins and conventional self-curing composite restorative materials to dentin surfaces of extracted human teeth was performed using the methods of this invention as described in Examples 1–4 hereinbelow in order to assess the effect of adhesion-promoting agents incorporating di- or polyvalent cations on adhesive bonding and tensile adhesive strength.

The following Examples illustrate certain aspects of the above-described method and advantageous results. The following examples are shown by way of illustration and not by way of limitation.

EXAMPLE 1

As a first step, one drop of 2.5% nitric acid solution was applied to the dentin surface. The surface was rubbed with a cotton pellet wetted with the same acid solution for 60 seconds and then excess liquid was blown off using a stream of air; care was taken so that the surface was not dried excessively. One drop of a 5% acetone solution of the magnesium salt or complex of NTG-GMA, an adhesion-promoting agent, was then applied to the surface. The surface was kept wet with this solution for 30 s, and then excess solvent was allowed to evaporate and the surface blown dry for 60 s. To the surface was then applied one drop of a 10% acetone solution of PMDM, an adhesive resin monomer, and the surface was kept wet with this solution for 30 s, after which time excess solvent was allowed to evaporate and the surface blown dry for 60 s. Finally, an unfilled light-cure resin was applied to the surface for 30 s, then blown thin with air and light cured for 30 s. An amount of conventional self-curing composite restorative material was then applied, and the average tensile adhesive bond strength tested after soaking in water for 1 day. The average adhesive bond strength to dentin with this testing protocol was 2,160 psi (pounds per square inch; 14.9 MPa, s=4.6, n=10), a result significantly higher than that of the first comparative control described in Example 2.

COMPARATIVE EXAMPLE 2

The adhesive bonding of tooth surfaces to conventional self-curing composite restorative material using the methods of this invention as described herein was compared with a method as disclosed in U.S. Pat. No. 4,964,911 in order to assess the differences in adhesive bonding and tensile adhesive strength between the present invention, employing di- or polyvalent cations, and a method employing monovalent cations.

Commercial samples of the adhesive bonding materials described in U.S. Pat. No. 4,964,911 were used according to the manufacturer's instructions. First, an aqueous solution of phosphoric acid or a mixture of phosphoric and nitric acids along with aluminum oxalate, or phosphoric acid alone, as supplied by the manufacturer, was applied to the surface to be bonded, following the manufacturer's directions. The surface was then rinsed thoroughly with water and dried under a stream of compressed air. Next, a solution comprising a solvent and a mixture of the adduct of N(p-tolyl)glycine and glycidyl methacrylate with its alkali metal salt and a solution of PMDM was applied to the surface, as supplied and directed by the manufacturer's directions. Finally, the same manufacturer's unfilled, light-curing resin was applied and light cured, as directed. Adhesive bond strengths of the resulting bonded surfaces were tested as described in Example 1. Using this method, a lower ranking average bond strength, compared with the methods of the present invention, was obtained: 680 psi (4.7 MPa, s=3.9, n=10). Because these results were lower than expected, the same protocol was repeated, except that the containers were shaken before dispensing; in this case the average bond strength was 1,400 psi (9.7 MPa, s=4.4, n=9). These results support the concept of this invention, that polyvalent cations can promote stronger bonding than monovalent cations to cleansed, superficially demineralized surfaces.

EXAMPLE 3

Another alternative embodiment of the present inventive method contains a step calling for treatment of the surface to be adhesively bonded with the lithium salt of p-toluene sulfinate. In the first step of this embodiment of the invention, one drop of 2.5% nitric acid solution was applied to the surface. The surface was rubbed with a cotton pellet wetted with the same acid solution for 60 s and then excess liquid was blown off using a stream of air; care was taken so that the surface was not dried excessively. One drop of a freshly-prepared solution of 2.5% lithium-p-toluene sulfinate in acetone/water (1:1) was then applied to the surface and allowed to stand undisturbed for 60 s before being dried gently with a stream of air. One drop of a 5% acetone solution of the magnesium salt or complex of NTG-GMA was then applied to the surface and let stand for 60 s then dried under a stream of compressed air. To the surface was then applied one drop of a solution of 15% PMGDM (the reaction product of pyromellitic dianhydride and glycerol dimethacrylate), 0.2% camphorquinone and 1.3% N,N-dimethylaminoethylbenzoate in acetone; the solvent allowed to evaporate for 50–60 s, the surface blown dry and light cured for 10 s. An amount of conventional self-curing composite restorative material was then applied, and the average tensile adhesive bond strength was tested in the usual manner after soaking in water for 1 day. Even without the use of a unfilled light-cured resin, which usually results in higher bond strengths, the average strength was 1,580 psi (10.9 MPa, s=2.0, n=10).

EXAMPLE 4

Additional di- and polyvalent salts or complexes of NTG-GMA were evaluated as adhesion-promoting agents in the same manner as in Example 1. The average tensile bond strengths obtained using these compounds were as follows: aluminum, 2,160 psi (14.9 MPa, s=6.1, n=10); zinc, 1,970 psi (13.6 MPa, s=4.9, n=9); calcium, 1,740 psi (12.0 MPa, s=5.3, n=10); and strontium, 1,540 psi (10.6 MPa, s=4.1, n=10). As can be seen from these results, using the methods of the present invention results in greater adhesive bond strengths than are obtained using methods employing monovalent cations of these adhesion-promoting agents.

EXAMPLE 5

In another set of comparative evaluations, after aqueous acidic cleansing, dentin was impregnated with acidic (zwitterionic) NTG-GMA or its Na, Mg, or other salt solutions in acetone and then with a PMDM (the adduct of pyromellitic dianhydride and hydroxyethyl methacrylate) acetone solution, followed by application of a composite resin. Mean (n=10) tensile bond strengths (see Bowen, J. Dent Res 71:615 abstract #796, 1992) were acidic NTG-GMA, 11.4 MPa (s=3.4); Na NTG-GMA, 12.9 (s=4.6); and Mg NTG-GMA, 14.9 (s=4.6). Average bond strength rankings and storage stability of solutions suggest further development and utilization of divalent and polyvalent cation salts or complexes of NTG-GMA.

It should be understood that the foregoing disclosure emphasizes certain specific embodiments of the invention and that all modifications or alternatives equivalent thereto are within the spirit and scope of the invention as set forth in the appended claims.

I claim:

1. A method for preparing the surface of dentin, enamel, or other natural or industrial substrates containing or capable of binding divalent or polyvalent cations or amines, for adhesion of composite materials or resins, which method comprises:

(a) contacting the surface with a solution comprising a composition having at least one acid, acidic salt, or chelating or sequestering agent, wherein the composition is soluble in water;

(b) contacting the surface with a solution comprising a composition having at least one adhesion-promoting agent selected from the group consisting of N-phenylglycine (NPG), N-phenylalanine, 2-(N-phenyl) alkanoic acids and derivatives and analogues thereof, and other amino acids, in the form of salts or complexes of these compounds with at least one member of the group consisting of divalent cations, polyvalent cations, amines, diamines and polyamines, wherein the composition is soluble in an organic solvent; and (c) contacting the surface with a liquid comprising at least one adhesive resin monomer selected from the group consisting of (1) reaction products of dianhydrides with molecules containing at least one methacrylate, acrylate or other polymerizable group and also one reactive hydroxyl group, or primary or secondary amino group, (2) 4-methacryloxyethyltrimelliticanhydride and its dicarboxylic acid hydrolysis derivative, (3) other compounds containing at least one group or moiety capable of free radical polymerization and at least one aromatic ring or moiety containing electron-withdrawing substituents that do not interfere with free radical polymerization, and (4) other compounds containing at least one group or moiety capable of free-radical polymerization and at least one carboxyl group or salt thereof.

2. The method of claim 1 wherein steps (a), (b) and (c) are performed in that order.

3. The method according to claim 1 wherein the divalent and polyvalent salts and complexes of subpart (b) are N-arylglycine and N-arylalanine derivatives and ring-substituted N-arylglycine and N-arylalanine derivatives, and wherein the derivatives contain at least one free carboxyl group and at least one polymerizable group.

4. The method according to claim 3 wherein the polymerizable group is a methacrylate, acrylate, vinyl or other group capable of free-radical polymerization.

5. The method of claim 1 wherein the monomer of subpart (c) is selected from the group consisting of (1) the addition reaction product of pyromellitic acid dianhydride and glyceroldimethacrylate, (2) the addition reaction product of 3,3',4,4'-benzophenonetetracarboxylic dianhydride and glyceroldimethacrylate, (3) 4-methacryloxyethyltrimellitic anhydride, and (4) trimellitic anhydride dimethacrylate.

6. The method of claim 1 wherein the concentration of acid, acidic salt, or chelating or sequestering agent is from about 0.1% to about 50%.

7. The method of claim 1 wherein the acid, acidic salt, or chelating or sequestering agent is in an aqueous solution which is substantially isotonic with physiological saline solution.

8. The method of claim 1 wherein the acid, acidic salt, or chelating or sequestering agent is selected from the group consisting of nitric acid, citric acid, phosphoric acid, hydrochloric acid, a sulfinic acid, formic acid, maleic acid, pyruvic acid and salts of ethylenediaminetetraacetic acid.

9. The method of claim 1 wherein the concentration of the monomer in the solution of subpart (c) is from about 0.1% to a saturated solution.

10. The method of claim 1 wherein the di- and polyvalent cations are cations of alkaline earth elements or transition metal elements or mixtures thereof.

11. The method of claim 1 wherein the solvent of subpart (c) is acetone.

12. The method of claim 1 wherein the substrate surface is a dentin surface or an enamel surface.

13. The method of claim 1 wherein the adhesion-promoting agent is N-phenylglycine.

14. The method of claim 1 wherein the adhesion-promoting agent is N-methyl-N-phenylglycine.

15. The method of claim 1 wherein the adhesion-promoting agent is N(p-tolyl)glycine.

16. The method of claim 1 wherein the adhesion-promoting agent is the adduct of N-phenylglycine and glycidyl methacrylate.

17. The method of claim 1 wherein the adhesion-promoting agent is the addition reaction product of N(p-tolyl)glycine and glycidyl methacrylate.

18. The method of claim 1 wherein the composition of subpart (b) also includes a composition comprised of a solvent and a polymerization initiator.

19. The method of claim 18 wherein the polymerization initiator is comprised of a salt or derivative of sulfinic acid.

20. The method of claim 18 wherein the polymerization initiator is applied to the substrate immediately before polymerization initiation is desired.

21. The method of claim 1 wherein one or more of the solutions of subparts (a)–(c) are mixed together immediately before application to the surface.

22. The method of claim 1 wherein at least one of the solutions of subparts (a)–(c) also contains at least one polymerization inhibitor.

23. The method of claim 22 wherein the polymerization inhibitor is selected from the group consisting of 4-hydroxymethyl-2,6-di-tert-butylphenol; BHT; 2,5-di-tert-butylhydroquinone; tert-butylhydroquinone; 4-hydroxy-3,5-di-tert-butylphenyl propionic acid; 3,3'-thiodipropionic acid; 3,5-di-tert-butyl-4-hydroxyanisole; the monomethyl ether of hydroquinone; and hydroquinone.

24. The method of claim 1 wherein at least one of the compositions of subparts (a)–(c) contains camphorquinone or a derivative of camphorquinone.

25. The method of claim 1 wherein at least one of the compositions of subparts (a)–(c) contains a tertiary amine having a hydrogen atom attached to a carbon atom adjacent to a nitrogen atom.

26. The method of claim 1 wherein at least one of the compositions of subparts (a)–(c) contains benzoyl or other peroxide.

27. The method of claim 1 wherein at least one of the compositions of subparts (a)–(c) contains an antimicrobial agent.

28. The method of claim 27 wherein the antimicrobial agent is a quaternary ammonium salt, a benzalkonium salt, a cetylpyridinium salt, a chlorhexidine salt or an alexidine salt.

29. A structure comprising a composite material or resin bonded to a dentin or enamel surface which has been prepared according to the method of claim 1.

30. A structure comprising a composite material or resin bonded to a natural or industrial substrate which has been prepared according to the method of claim 1.

31. A method for bonding a composite material or resin to the surface of dentin, enamel, or other natural or industrial substrates containing or capable of binding divalent or polyvalent cations or amines which comprises practicing the method of claim 1, and then contacting the surface with an unfilled light-cure resin and light-curing the resin.

32. A method for preparing the divalent and polyvalent salts and complexes of adhesion-promoting agents of subpart (b) of claim 1 comprising:
(a) providing a first solution comprised of monovalent cationic salts or ammonium or amine salts of at least one adhesion-promoting agent selected from the group consisting of N-phenylglycine (NPG), and derivatives and analogues thereof, and other amino acids;
(b) providing a second concentrated solution of at least one salt of magnesium, calcium, aluminum, strontium, zinc, barium, iron, chromium, manganese, cobalt, copper, molybdenum, other di- or polyvalent cations, amine salts, or quaternary ammonium compounds, or mixtures thereof, wherein these salts do not form totally insoluble reaction products with the compounds of subpart (a);
(c) mixing the first and second solutions by stirring to form a precipitate of divalent or polyvalent salts and complexes thereof; and
(d) separating the precipitate from the solution.

33. A method for preparing the surface of dentin, enamel, or other natural or industrial substrates containing or capable of binding divalent or polyvalent cations or amines, for adhesion of composite materials or resins, which method comprises:
(a) contacting the surface with a solution comprising a composition having at least one acid, acidic salt, or chelating or sequestering agent, wherein the composition is soluble in water;
(b) contacting the surface with a solution comprising a composition having at least one adhesion-promoting agent selected from the group consisting of N-phenylglycine (NPG), N-phenylalanine, 2-(N-phenyl) alkanoic acids and derivatives and analogues thereof, and other amino acids, in the form of salts or complexes of these compounds with at least one member of the group consisting of divalent cations, polyvalent cations, amines, diamines and polyamines, wherein the composition is soluble in an organic solvent; and
(c) contacting the surface with a liquid comprising at least one adhesive resin monomer selected from the group consisting of (1) reaction products of dianhydrides with molecules containing at least one methacrylate, acrylate or other polymerizable group and also one reactive hydroxyl group, or primary or secondary amino group, (2) 4-methacryloxyethyltrimelliticanhydfide and its dicarboxylic acid hydrolysis derivative, and (3) other compounds containing at least one group or moiety capable of free radical polymerization and at least one aromatic ring or moiety containing electron-withdrawing substituents that do not interfere with free radical polymerization.

34. A method for preparing the surface of dentin, enamel, or other natural or industrial substrates containing or capable of binding divalent or polyvalent cations or amines, for adhesion of composite materials or resins, which method comprises:
(a) contacting the surface with a solution comprising a composition having at least one acid, acidic salt, or chelating or sequestering agent, wherein the composition is soluble in water;
(b) contacting the surface with a solution comprising a composition having at least one adhesion-promoting agent selected from the group consisting of N-phenylglycine (NPG), N-phenylalanine, 2-(N-phenyl) alkanoic acids and derivatives and analogues thereof, and other amino acids, in the form of salts or complexes of these compounds with at least one member of the group consisting of divalent cations, polyvalent cations, amines, diamines and polyamines, wherein the composition is soluble in an organic solvent; and p1 (c) contacting the surface with a liquid comprising at least one adhesive resin monomer selected from the group consisting of reaction products of dianhydrides with molecules containing at least one methacrylate, acrylate or other polymerizable group and also one reactive hydroxyl group, or primary or secondary amino group, wherein the dianhydrides are selected from one or more of the group consisting of 5-(2,5-dioxotetrahydro-3-furanyl)-3-cyclohexene-1,2-dicarboxylic anhydride, symmetrical biphenyl tetracarboxylic dianhydride, glycerol acetate bistrimellitate dianhydride, polyol trimellitate dianhydride, 3,3',4,4'-diphenylsulfone tetracarboxylic dianhydride, 4,4'-oxydiphthalic anhydride, 4,4'-hexafluoroisopropylidene-bisphthalic anhydride, pyromellitic dianhydride, 3,3',4,4'-benzophenone tetracarboxylic dianhydride, ethylene glycol bistrimellitate dianhydride, mellophanic dianhydride, bicyclo(2.2.2)octane-2,3,5,6-tetracarboxylic dianhydride, bicyclo(2.2.2)-7-octene-2,3,5,6-tetracarboxylicdianhydride, and 1,2,3,4-cyclopentanetetracarboxylic dianhydride.

35. A method for preparing the surface of dentin, enamel, or other natural or industrial substrates containing or capable of binding divalent or polyvalent cations or amines, for adhesion of composite materials or resins, which method comprises:
  (a) contacting the surface with a solution comprising a composition having at least one acid, acidic salt, or chelating or sequestering agent, wherein the composition is soluble in water;
  (b) contacting the surface with a solution comprising a composition having at least one adhesion-promoting agent selected from the group consisting of N-phenylglycine (NPG), N-phenylalanine, 2-(N-phenyl) alkanoic acids, N-phenylalanine, 2-(N-phenyl) alkanoic acids other amino acids, and derivatives and analogues thereof selected from the group consisting of the addition reaction product of N(p-tolyl)glycine and glycidyl methacrylate (NTG-GMA); the adduct of N-phenylglycine and glycidyl methacrylate (NPG-GMA); the adduct of N(4-chlorophenyl)glycine and glycidyl methacrylate (NCPG-GMA); the adduct of N-phenylglycine and 1,2-epoxy-3-phenoxypropane (NPG-PGE); the adduct of N-phenylglycine and p-chlorophenyl-2,3-epoxypropyl ether (NPG-CGE); the adduct of N-p-chlorophenylglycine and p-chlorophenyl-2,3-epoxypropyl ether (NCG-CGE); the reaction product of N-p-chlorophenylglycine and phenyl-2,3-epoxypropyl ether (NCG-PGE); the adduct of N-phenylalanine and glycidyl methacrylate (NPA-GMA); and the adduct of N-tolyl-2(or alpha)-alanine, N-phenylalanine or 2-(N-phenyl) alkanoic acids and glycidyl methacrylate (NTA-GMA), in the form of salts or complexes of these compounds with at least one member of the group consisting of divalent cations, polyvalent cations, amines, diamines and polyamines, wherein the composition is soluble in an organic solvent; and
  (c) contacting the surface with a liquid comprising at least one adhesive resin monomer selected from the group consisting of (1) reaction products of dianhydrides with molecules containing at least one methacrylate, acrylate or other polymerizable group and also one reactive hydroxyl group, or primary or secondary amino group, (2) 4-methacryloxyethyltrimelliticanhydride and its dicarboxylic acid hydrolysis derivative, (3) other compounds containing at least one group or moiety capable of free radical polymerization and at least one aromatic ring or moiety containing electron-withdrawing substituents that do not interfere with free radical polymerization, and (4) other compounds containing at least one group or moiety capable of free-radical polymerization and at least one carboxyl group or salt thereof.

36. A method for preparing the surface of dentin, enamel, or other natural or industrial substrates containing or capable of binding divalent or polyvalent cations or amines, for adhesion of composite materials or resins, which method comprises:
  (a) contacting the surface with a solution comprising a composition having at least one acid, acidic salt, or chelating or sequestering agent, wherein the composition is soluble in water;
  (b) contacting the surface with a solution comprising a composition having at least one adhesion-promoting agent selected from the group consisting of N-phenylglycine (NPG), N-phenylalanine, 2-(N-phenyl) alkanoic acids and derivatives and analogues thereof, and other amino acids, in the form of salts or complexes of these compounds with at least one member of the group consisting of divalent cations, polyvalent cations, amines, diamines and polyamines, wherein the composition is soluble in an organic solvent, and wherein the divalent and polyvalent salts or complexes of N-phenylglycine (NPG), and derivatives and analogues thereof are substantially in the form of salts and complexes selected from the group consisting of amine, diamine, polyamine, calcium, aluminum, magnesium, strontium, zinc, barium, iron, chromium, manganese, cobalt, copper and molybdenum salts, and
  (c) contacting the surface with a liquid comprising at least one adhesive resin monomer selected from the group consisting of (1) reaction products of dianhydrides with molecules containing at least one methacrylate, acrylate or other polymerizable group and also one reactive hydroxyl group, or primary or secondary amino group, (2) 4-methacryloxyethyltrimelliticanhydride and its dicarboxylic acid hydrolysis derivative, (3) other compounds containing at least one group or moiety capable of free radical polymerization and at least one aromatic ring or moiety containing electron-withdrawing substituents that do not interfere with free radical polymerization, and (4) other compounds containing at least one group or moiety capable of free-radical polymerization and at least one carboxyl group or salt thereof.

37. The method of claim 36 wherein the amines are ammonia, primary, secondary or tertiary amines.

38. The method of claim 37 wherein the amines are hexamethylenetetramine; 1,4-diazabicyclo[2.2.2]octane; quinuclidine; N,N-diethylethanolamine; N-ethyldiethanolamine; triethanolamine; N,N-dihydroxy-p-toluidine; 3-quinuclidinol; N,N-dihydroxyethylglycine; N,N-dimethylglycine; 2-quinuclidine carboxylic acid; N,N-dimethylaminoethylmethacrylate; or N, N-diethylaminoethylmethacrylate.

39. A method for preparing the di- and polyvalent salts and complexes of adhesion-promoting agents of subpart (b) of claim 1 comprising: (a) condensing divalent or polyvalent cation salts of 2-haloalkanoic acids with amines selected from the group consisting of aniline, ring-substituted derivatives and analogues of aniline, and amino acids, which salts do not undergo adverse interactions or form totally insoluble reaction products;
  (b) optionally reacting said reaction products with compounds containing alkylating moieties and polymerizable groups, and
  (c) separating the precipitated divalent and polyvalent salts and complexes of adhesion-promoting agents from the solution.

* * * * *